(12) United States Patent
Murakami et al.

(10) Patent No.: US 8,340,739 B2
(45) Date of Patent: Dec. 25, 2012

(54) MONITOR DEVICE AND BIOLOGICAL COMPONENT-MEASURING DEVICE

(75) Inventors: Motoaki Murakami, Makinohara (JP); Yoshihiko Izumichi, Makinohara (JP)

(73) Assignee: Nikkiso Co., Ltd., Tokyo (JP)

( * ) Notice: Subject to any disclaimer, the term of this patent is extended or adjusted under 35 U.S.C. 154(b) by 791 days.

(21) Appl. No.: 12/524,028

(22) PCT Filed: Jan. 25, 2008

(86) PCT No.: PCT/JP2008/000093
§ 371 (c)(1),
(2), (4) Date: Jul. 22, 2009

(87) PCT Pub. No.: WO2008/093494
PCT Pub. Date: Aug. 7, 2008

(65) Prior Publication Data
US 2010/0028989 A1    Feb. 4, 2010

(30) Foreign Application Priority Data

Jan. 30, 2007   (JP) ................................ 2007-020212

(51) Int. Cl.
*A61B 5/00*       (2006.01)
*A61M 37/00*      (2006.01)
*C12M 1/34*       (2006.01)
*C12M 3/00*       (2006.01)

(52) U.S. Cl. ....... 600/316; 600/325; 600/365; 604/4.01; 435/288.7

(58) Field of Classification Search .................. 600/316, 600/322–325, 328, 365; 604/4.01, 5.01, 604/5.04, 6.09, 6.11; 435/288.7
See application file for complete search history.

(56) References Cited

U.S. PATENT DOCUMENTS

2008/0015487 A1* 1/2008 Szamosfalvi et al. ....... 604/6.07

FOREIGN PATENT DOCUMENTS

| JP | 10-19832 A | 1/1989 |
|----|------------|--------|
| JP | 1-152357 A | 6/1989 |
| JP | 8-327587 A | 12/1996 |
| JP | 8-332180 A | 12/1996 |
| JP | 11-000317 A | 1/1999 |
| JP | 2000-245825 A | 9/2000 |

\* cited by examiner

*Primary Examiner* — Rochelle-Ann J Blackman
(74) *Attorney, Agent, or Firm* — McDermott Will & Emery LLP (57) ABSTRACT

This invention provides a monitor device capable of detecting possible abnormalities in body fluid withdrawal by a body fluid sampler and variations in the dilution when a withdrawn body fluid is diluted, and a living organism-measuring device with this monitor device. The former device includes a first optical sensor disposed on a diluent channel through which a diluent is introduced into a body fluid sampler for withdrawing a body fluid; a second optical sensor disposed on a diluted body fluid channel through which the diluted body fluid is transferred to a living organism-measuring sensor, and close to the first optical sensor; and a controlling unit for judging whether variations in a dilution to which the body fluid is diluted are within predetermined limits, from data outputted by the first optical sensor and data outputted by the second optical sensor. The latter device has the monitor device incorporated thereto.

9 Claims, 2 Drawing Sheets

MONITOR DEVICE AND BIOLOGICAL COMPONENT-MEASURING DEVICE

CROSS-REFERENCE TO PRIOR APPLICATION

This is the U.S. National Phase Application under 35 U.S.C. §371 of International Patent Application No. PCT/JP2008/000093 filed Jan. 25, 2008, which claims the benefit of Japanese Patent Application No. 2007-020212 filed Jan. 30, 2007, both of which are incorporated by reference herein. The International Application was published in Japanese on Aug. 7, 2008 as WO2008/093494 A1 under PCT Article 21(2).

TECHNICAL FIELD

The present invention relates to a monitor device and a biological component-measuring device. More particularly, the present invention relates to a monitor device capable of accurately monitoring dilution when a body fluid withdrawn from a living organism is diluted with a diluent, and a biological component-measuring device, such as artificial endocrine pancreas devices, equipped with the monitor device, capable of measuring an amount of a target component, such as a blood sugar level in body fluids, especially in blood.

BACKGROUND ART

Biological component-measuring devices that have been used in the hospital are sometimes used continuously for a long time. Biological component-measuring devices used in this manner have problems, such as variation of measured values that increases with time, caused by deterioration. Devices, such as artificial endocrine pancreas devices, which carry out a closed loop control where components in the blood, a body fluid, of a patient, such as glucose, are measured continuously or at intervals, and liquid medicines such as insulin are injected into the patient based on the measurement in order to control the patient's conditions, require accurate and safe operation during their use, often over a long period of time. Specifically, it is said that an artificial endocrine pancreas device should be capable of providing accurate measurement for a period from about four hours to about one week.

When biological components such as glucose in a body fluid such as blood are measured, the body fluid withdrawn from a living organism is usually diluted with a diluent including a mixture of physiological saline and an anticoagulant, prior to the measurement. With artificial endocrine pancreas devices that are used for a long time, deterioration in device parts and abnormal blood withdrawal sometimes cause changes in dilution. These changes in the dilution directly affect measured values, or result in errors in a measurement of a biological component. If the doctor does not notice problems such as abnormal blood withdrawal during the monitoring, there is a probability that s/he regards the measured values with errors as accurate values and injects liquid medicines into the patient based on them.

In these situations are demanded biological component-measuring devices capable of continuously detecting changes in the dilution without imposing burden to patients, which enables the doctor to deal with problems such as abnormal blood withdrawal.

Patent document 1 discloses an automatic blood-pressure measuring device, though not a biological component-measuring device.

The automatic blood-pressure measuring device disclosed in Patent document 1 comprises a blood-pressure meter with a cuff wherein a blood pressure value of a living organism is measured by changing a squeezing pressure applied to a part of the living organism with the cuff, a hematocrit detector for continuously detecting a hematocrit value of the living organism, and a blood-pressure measurement actuator for automatically actuating the blood-pressure meter to measure a blood pressure of the living organism when a detected hematocrit value exceeds a preset reference value. See claim 1 of Patent document 1.

An example of the hematocrit detector included in the automatic blood-pressure measuring device of Patent document 1 is an optical noninvasive hematocrit sensor 72. Patent document 1 includes the following teaching about the optical noninvasive hematocrit sensor 72: "The sensor is equipped with a sensor clip 74 that includes a built-in light-emitting device for irradiating blood with a light beam having a predetermined wavelength, and a built-in light-detecting device for detecting light traveling through the blood and light scattered by the blood. The sensor clip 74 is fitted to a transparent container of the drip chamber 62 so that the container is held on with the sensor clip. The optical noninvasive hematocrit sensor calculates hematocrit values Ht in succession from the light detected by the light-detecting device, and continuously sends the calculated values to an inlet port 38 of the electronic controller 28. Because the hematocrit value Ht of a blood sample means a volume percent (%) of blood corpuscles in the sample, an increase in the hematocrit value means a decrease in the blood plasma whose percent by volume is obtained by subtracting the percent by volume of blood corpuscles from 100, represented by the equation (100−Ht) %." See paragraph [0014] of Patent document 1.

Concerning the hematocrit value, Patent document 1 teaches the following: "The hematocrit value Ht of the blood of a dialysis patient, obtained from a signal outputted by a hematocrit sensor 72, is sent to the blood-pressure measurement actuator. Then, at step SA4 that corresponds to processing with the blood-pressure measurement actuator 84, the actuator judges whether or not the measured hematocrit value Ht is larger than a predetermined reference value A (%), or the percent by volume of the blood plasma of the dialysis patient is smaller than the criterion (100−A) %." See paragraph [0022] of Patent document 1.

The teaching continues: "When the judgment at step SA4 is negative, the current routine is completed. On the other hand, when the judgment is positive, step SA5 and the following steps are carried out in the same way as the manual actuating operation explained above is carried out. As a result, a blood pressure measurement of the dialysis patient is automatically started, triggered by an increase in the hematocrit value Ht. See paragraph [0023] of Patent document 1.

The automatic blood-pressure measuring device disclosed in Patent document 1 boasts technical advantages thereof as follows: "As explained hereinbefore, the device of this working example has the blood-pressure measurement actuator 84 that enables the blood-pressure meter 80 to automatically start a blood-pressure measurement (at step SA9) when the actuator judges (at step SA4) that any one of the hematocrit values Ht continuously detected by the hematocrit sensor 72 exceeds a predetermined criterion A. In other words, the device of the invention is capable of measuring the blood-pressure value of a dialysis patient when the volume of the blood plasma circulating through the patient decreases, which enables the doctor to quickly provide the patient with medical treatment to deal with the blood pressure decrease." See paragraph [0024] of Patent document 1.

Especially remarkable in the device disclosed in Patent document 1 are that the hematocrit sensor is a combination of the light-emitting device and the light-detecting device which are disposed so that they hold the drip chamber between them and that the percent by volume of blood corpuscles is obtained based on detection data outputted by the light-detecting device. Also, a decrease in the blood pressure of a patient during dialysis is predicted based on hematocrit values which represent the proportion (%) of the volume of blood corpuscles to that of the entire blood, and which values are measured by the optical method, in the invention disclosed in Patent document 1.

However, a prerequisite for measurement of the proportion of the volume of blood corpuscles to that of the blood with the automatic blood-pressure measuring device disclosed in Patent document 1, equipped with a combination of a light-detecting device and a light-emitting device is that blood withdrawn from a patient flows through an extracorporeal blood-circulating path 68. If the tip of an indwelling needle kept in a vein of a patient 58 is stopped up for some reason such as a contact of its opening end to the vascular wall, or a clog of blood adhering to the opening end of the indwelling needle or the inner wall of the circulating path therein, which results in prevention or blockage of the blood circulation, the blood of the patient 58 is not withdrawn properly though apparently blood is withdrawn from the patient 58 at a predetermined flow rate. Hematocrit values obtained in such a state do not represent accurate values of a dialysis patient, so that his/her blood pressure cannot be measured accurately. Another problem associated with this method is that measurement with a light-emitting device and a light-detecting device is prone to be affected by external disturbing factors such as variations in the temperature and incoming light beams, especially direct rays of the sun.

Patent document 1: JP H11-317 A (1999)

DISCLOSURE OF THE INVENTION

Problems to be Solved by the Invention

An objective of the present invention is to provide a monitor device capable of detecting possible abnormalities in body fluid withdrawal by a body fluid sampler and variations in the dilution when a withdrawn body fluid is diluted with a diluent. The present invention also provides a biological component-measuring device, such as an artificial endocrine pancreas device, equipped with this monitor device, capable of properly dosing patients, such as those who are in a state of surgical hyperglycemia after invasions by surgical operations or diseases and/or injuries, those of diabetes mellitus, and those in a state of hypoglycemia caused by diseases and/or injuries such as insulinoma, with hormones capable of varying the blood sugar level, such as insulin, glucose or glucagons, medical fluids or medicines.

Means to Solve the Problems

In order to achieve the objective written above, the present invention provides the following means.

The first means is a monitor device including:
a first optical sensor disposed on a diluent channel through which a diluent is introduced into a body fluid sampler for withdrawing a body fluid;
a second optical sensor disposed on a diluted body fluid channel through which a diluted body fluid is transferred to a biological component-measuring sensor, and in close proximity to the first optical sensor, wherein the diluted body fluid is prepared by mixing the body fluid withdrawn by the body fluid sampler with the diluent; and
a controlling unit for judging whether variations in a dilution to which the body fluid is diluted with the diluent is within predetermined limits, based on first detection data outputted by the first optical sensor and second detection data outputted by the second optical sensor.

The second means is a biological component-measuring device including the monitor device according to the first means.

The third means is a biological component-measuring device according to the second means, further including a diluted standard solution-supplying unit comprising:
a diluent-supplying channel branched from the diluent channel via a first flow path changeover device at a location downstream of the first optical sensor;
a standard solution-diluting unit for diluting a standard solution with the diluent introduced thereto through the diluent-supplying channel to prepare a diluted standard unit; and
a diluted standard solution-drawing channel branched from the diluted body fluid channel via a second flow path changeover device at a location upstream of the second optical sensor wherein the diluted standard solution prepared in the standard solution-diluting unit is drawn and sent to the diluted body fluid channel through the diluted standard solution-drawing channel.

The fourth means is the biological component-measuring device according to the second or third means wherein the biological component-measuring device is applied to an artificial endocrine pancreas device.

Advantages of the Invention

A detected datum outputted by the second optical sensor when the monitor device whose second optical sensor is not disposed on the diluted body fluid channel is operated is essentially the same as a voltage A, or a detected datum, outputted by the second optical sensor when the monitor device whose optical sensor is disposed on the diluted body fluid channel through which the diluted body fluid does not flow is operated. However, a voltage B outputted by the second optical sensor when the monitor device whose second optical sensor is disposed on the diluted body fluid channel through which a liquid that does not contain a component to be measured at all, such as water or physiological saline, flows is larger than the voltage A. Therefore the voltage B can be distinguished from the outputted voltage A.

Also, when a liquid that is not diluted at all, such as a body fluid per se, flows through the diluted body fluid channel, a voltage C, or a detected datum outputted by the second optical sensor, is smaller than the voltage B.

When a diluted body fluid made by diluting a body fluid with a diluent so as to achieve a constant dilution flows through the diluted body fluid channel, a voltage as a detected datum outputted by the second optical sensor is between the voltage B and the voltage C.

Therefore it cannot be understood only from detected data outputted by the second optical sensor whether a diluted body fluid flows through the diluted body fluid channel.

Detected data outputted by the second optical sensor of the monitor device according to the present invention include noises. Therefore you can judge whether the data are of a diluted body fluid or not from existence or non-existence of noises in the outputted voltage.

On the other hand, second detected data outputted by the second optical sensor are not constant but variable as time, affected by external disturbing factors such as changes in the temperature, irradiation with light beams entering from the outside, especially direct rays of the sun, and/or transmission of light beams through fluid in the channel when the concentration of the fluid is small. The dilution cannot be monitored accurately only from the detection data outputted by the second optical sensor. The monitor device according to the present invention carries out an optical measurement of a diluted body fluid flowing through the diluent channel with the second optical sensor, and an optical measurement of a diluent flowing through the diluted body fluid channel with the first optical sensor. Because first data outputted by the first optical sensor and second data outputted by the second optical sensor are simultaneously affected by the external disturbing factors, a subtraction of the first data from the second data will cancel out the influence by the external disturbing factors included in the second data. Thus the dilution of the diluted body fluid is calculated from the result of the subtraction by the controlling unit. The monitor device according to the present invention monitors whether the dilution of the diluted body fluid outputted by the controlling unit is within a predetermined range.

Thus the present invention provides a monitor device capable of judging whether a withdrawn body fluid is diluted with a diluent to a predetermined dilution, or finding abnormalities in the dilution. Specifically, according to the present invention, the monitor device thus provided is capable of detecting possible abnormalities in withdrawing body fluids by a body fluid sampler and variations in dilution when a withdrawn body fluid is diluted with a diluent.

A biological component-measuring device equipped with this monitor device according to the present invention is capable of continuously monitoring the dilution of a body fluid during an operation of this device, and quickly finding abnormalities in the dilution due to various reasons including anything unusual that has happened during the withdrawal of a body fluid by the body fluid sampler when the monitored dilution of the body fluid, which should have been diluted to a dilution within a predetermined range, is outside the range. As a result, the biological component-measuring device enables the doctor to provide the patient with an appropriate medical treatment based on the results of an analysis of the components and/or properties of the withdrawn body fluid.

Therefore, the present invention provides a biological component-measuring device which is capable of continuously monitoring whether a body fluid withdrawn from a patient is diluted to a predetermined dilution during an operation of this device, and enables the operator to deal with causes of the detected abnormalities, such as abnormal blood withdrawal. Specifically, the present invention provides a biological component-measuring device capable of properly dosing patients, such as those who are in a state of surgical hyperglycemia after invasions by surgical operations or diseases and/or injuries, those of diabetes mellitus, and those in a state of hypoglycemia caused by diseases and/or injuries such as insulinoma, with hormones capable of varying the blood sugar level, such as insulin, glucose or glucagons, medical fluids or medicines.

When a biological component-measuring device according to the present invention is provided with a diluted standard solution-supplying unit, it is capable of accurately measuring living organisms, specifically body fluids thereof, with the monitor device described hereinbefore.

When the biological component-measuring device of the invention is applied to an artificial endocrine pancreas device, the device is capable of quickly detecting abnormal blood withdrawal. If the device is further equipped with the diluted standard solution-supplying unit, the device is capable of accurately measuring a blood sugar level.

EXPLANATION OF REFERENCE NUMERALS 1 monitor device
2 first optical sensor
3 second optical sensor
4 controlling unit
5 diluent tank
6 body fluid sampler
7 diluent channel
8 biological component-measuring sensor
9 diluted body fluid channel
10 diluent-pumping device
11 diluted body fluid-pumping device
12 display
20 biological component-measuring device
21 diluted standard solution-supplying unit
22 first flow path changeover device
23 diluent-supplying unit
24 standard solution-diluting unit
25 second flow path changeover device
26 diluted standard solution-drawing channel
27 standard solution tank
28 waste liquid tank

BEST MODE TO CARRY OUT THE INVENTION

We will explain the present invention herein after, referring to examples shown in the figures.

Figure 1:
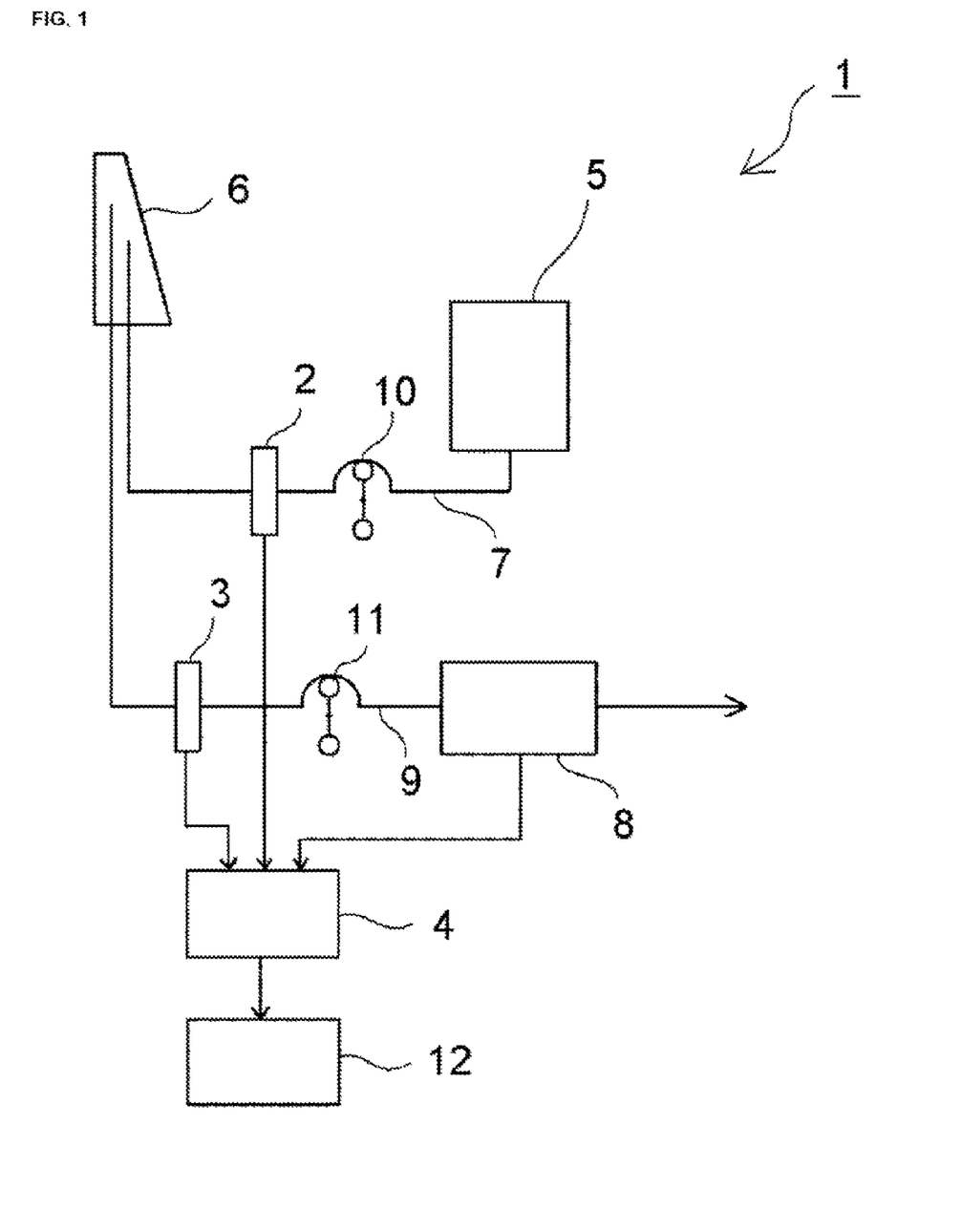
FIG. 1 is an illustration depicting an example of the monitor device according to the present invention.

As shown in FIG. 1, a monitor device 1, which is an example according to the present invention, includes a first optical sensor 2, a second optical sensor 3 and a controlling unit 4.

The first optical sensor 2 is fitted to a diluent channel 7 through which a diluent stored in a diluent tank 5 is sent to a body fluid sampler 6. The first optical sensor 2 has a combination of a light-emitting device and a light-detecting device disposed on the diluent channel 7 with the channel in between, so that a light beam emitted by the light-emitting device passes through the inside of the diluent channel 7 and is detected by the light-detecting device, which outputs a voltage as a detection datum and sends it to the controlling unit 4. The light-emitting device 2 may be either a photocoupler type or a photointerrupter type. The photointerrupter may be either a transmissive type or a reflective type. For the device shown in FIG. 1 is appropriate a combination of a near-infrared light-emitting device, which emits near-infrared light, and a near-infrared light-detecting device, which detects near-infrared light. Monitor devices equipped with a combination of a near-infrared light-emitting device and a near-infrared light-detecting device are capable of obtaining a lot of information about examined living organisms, such as concentrations of various biological components, examples of which include hemoglobin, glucose, urea and creatinine. Also, the combination is appropriate for detection of components included in a fluid flowing through the inside of a disposable medical product, because detection results are hardly affected by visible light and near-infrared light easily passes through resins. The part of the diluent channel 7 to which the first optical sensor 2 is fitted is made so that the part transmits light.

A diluent is stored in the diluent tank 5. The diluent may be anything, as long as it does not affect living organisms adversely, interfere with optical measurement by the first optical sensor 2 and the second optical sensor 3, change a body fluid in its properties, or coagulate a body fluid. Preferable examples of the diluent may include a physiological saline, Ringer's solution, distilled water and a phosphate buffer. In order to prevent a body fluid such as blood from gelling at the tip of the body fluid sampler such as a catheter 6, Ringer's solution, the physiological saline, the distilled water into which an anticoagulant is incorporated may be used preferably. Examples of the anticoagulant may include heparin, Nafamostat mesylate and urokinase.

The diluent channel 7 is provided with a diluent-pumping device 10. The diluent-pumping device 10, once actuated, drives a diluent in the diluent tank 5 out of the tank to the body fluid sampler 6.

The diluent-pumping device 10 should preferably be a pump with a function of preventing backflow. Preferable examples of the pump may include tube pumps or linear peristaltic pumps with this function.

For the body fluid sampler 6 may be employed those so structured that they are capable of withdrawing a body fluid, for example blood, and mixing the blood with a diluent introduced into the sampler through the diluent channel 7. Examples of the body fluid sampler may include catheters, particularly double lumen catheters.

The second optical sensor 3 is fitted to a diluted body fluid channel 9, through which a diluted body fluid, a mixture of a body fluid withdrawn by the body fluid sampler 6 and a diluent, is sent to a biological component-measuring sensor 8. The second optical sensor is also located in close proximity to the first optical sensor 2.

The diluted body fluid channel 9 is provided with a diluted body fluid-pumping device 11. The diluted body fluid-pumping device 11 may have the same structure as the diluent-pumping device 10 explained hereinbefore.

The second optical sensor 3 may have the same structure as the first optical sensor 2. Specifically, the second optical sensor 3 has a combination of a light-emitting device for irradiating a diluted body fluid that flows through the diluted body fluid channel 9 with a light beam and a light-detecting device disposed on the diluted body fluid channel 9 with the channel 9 in between, for detecting light that has passed through the diluted body fluid and outputting detection data. The detection data are outputted in the form of voltage, which is sent to the controlling unit 4.

When the second optical sensor 3 and the first optical sensor 2 are disposed in close proximity to each other, external disturbing factors that affect the first optical sensor 2 are considered the same as external disturbing factors that affect the second optical sensor 3. An embodiment to achieve the close proximity of the first optical sensor 2 to the second optical sensor 3 may be a structure including a single substrate on which the diluent channel 7 with the first optical sensor 2, and the diluted body fluid channel 9 with the second optical sensor 3 are arranged. The substrate may be any member as long as it is capable of having thereon the first optical sensor 2 fitted to the diluent channel 7 and the second optical sensor 3 fitted to the diluted body fluid 9 in the same conditions or essentially the same conditions. The member may sometimes be called by appropriate names other than substrate, such as mounting plate, placing plate, or member for arrangement.

The biological component-measuring sensor 8 may include sensors capable of measuring components and/or properties of a body fluid. The body fluid includes, for example, blood, urine, lymph or cerebrospinal fluid, or mixtures thereof. The components included in a body fluid, the qualitative or quantitative analysis of which is necessary for medical practice, may include glucose, urea, uric acid, lactose, sucrose, lactate (or lactic acid), ethanol, glutamic acid, ammonia, creatinine, and oxygen. Properties of a body fluid to be measured may include a pH value and an oxygen concentration thereof.

For the biological component-measuring sensor 8 may be employed various sensors depending on the components to be measured. Examples of such sensors may include biosensors, such as enzyme sensors utilizing enzymes, microorganism sensors employing microorganisms, and hybrid sensors utilizing enzymes and microorganisms. The enzyme or microorganism utilized in such a biosensor is selected depending on the target to be measured, or the biological component. For example, when the target to be measured is glucose, β-D-glucose oxidase or *Pseudomonas fluorecens* may be employed as biosensor. When the target is urea, urease may be employed as biosensor; when the target is uric acid, uricase may be employed; for lactate may be used lactate oxidase; for lactose may be employed lactase or β-galactosidase; for ethanol may be employed alcohol oxidase or *Trichosporon brassicaes*; for glutamic acid may be employed glutamate dehydrogenase or *Escherichia coli*; and for ammonia may be employed nitrifying bacteria.

The controlling unit 4 is capable of calculating the dilution of a diluted body fluid flowing through the diluted body fluid channel 9 from a first voltage, a first detection datum outputted by the first optical sensor 2, and a second voltage, a second detection datum outputted by the second optical sensor 3; judging whether or not the body fluid withdrawal is carried out normally; and checking whether the first optical sensor 2 is fitted to the diluent channel 7. These functions of the controlling unit 4 may be provided by a computer.

More specifically, when first voltages outputted by the first optical sensor 2 are not scattered or varied, the controlling unit 4 judges that the first optical sensor 2 is not fitted to the diluent channel 7, or a diluent does not flow through the diluent channel 7 even if the first optical sensor 2 is fitted to the channel 7. In other words, when first voltages outputted by the first optical sensor 2 are not varied, the controlling unit judges that the first optical sensor 2 is not ready to measure a diluent flowing through the diluent channel 7. The controlling unit produces a command based on this judgment and sends it to a display 12. Upon the receipt of the command sent by the controlling unit 4, the display 12, such as a CRT, displays a warning.

When first voltages, or first detection data outputted by the first optical sensor 2 that is fitted to the diluent channel 7, and second voltages, or second detection data outputted by the second optical sensor 3 that is fitted to the diluted body fluid channel 9, are inputted to the controlling unit 4, the controlling unit removes the external disturbing factors by correcting the second detection data by the corresponding first detection data that are used as reference data, and calculates variations in the dilution to which a withdrawn body fluid is diluted with the diluent.

The monitor device according to the present invention calculates variations in the dilution in the following way: When a diluent is allowed to flow through the diluent channel 7, let the first voltage as the detection datum outputted by the first optical sensor 2 at the beginning of the flowing be denoted by Vs(0), and let a first voltage as a detection datum outputted by the first optical sensor 2 when a period of time t lapses from the beginning be denoted by Vs(t). When a diluted body fluid, or a body fluid diluted with the diluent, is allowed to flow through the diluted body fluid channel 9, let the second voltage as the detection datum outputted by the second optical sensor 3 at the beginning of the flowing of the diluted body fluid be denoted by Vb(0), and a second voltage outputted as a detection datum by the second optical sensor 3 when a period of time t lapses from the beginning be denoted by Vb(t). In these conditions, ΔV denoting a variation in the voltage is expressed by one of ΔV1 calculated by equation (1), ΔV2 calculated by equation (2), and ΔV3 calculated by equation (3).

$$\Delta V1 = (Vb(t)/Vs(t))/(Vb(0)/Vs(0)) \quad (1)$$

$$\Delta V2 = \log(Vb(t)/Vs(t)) \quad (2)$$

$$\Delta V3 = \log[(Vb(t)-Vb0(t)/(Vs(t)-Vs0(t))] \quad (3)$$

In equation (3) Vb0(t) and Vs0(t) respectively denote a first voltage outputted by the first optical sensor and a second voltage outputted by the second optical sensor when the output powers of the first and second light-emitting devices are nullified just after the lapse of a time period t. These voltages represent an influence by external disturbing factors. The subtraction of Vb0(t) and Vs0(t) respectively from Vb(t) and Vs(t) will cancel out the influence by incoming light from the outside, which incoming light hampers materialization of Beer's law.

The controlling unit of the monitor device according to the present invention judges whether variations in the dilution are in the range of a predetermined lower limit to a predetermined upper limit. When variations are found within the range, the controlling unit decides that a body fluid is diluted with a diluent to a predetermined dilution. On the other hand, when variations are over the upper limit or under the lower limit, the controlling unit judges that a body fluid is not diluted to a predetermined dilution. Then, the controlling unit 4 outputs the judgment, which is shown on the display 12 such as a screen of a CRT.

The monitor device according to the present invention operate in the following way: The diluent pumping device 10 draws a diluent stored in the diluent tank 5 and sends it through the diluent channel 7 to the body fluid sampler 6. The body fluid sampler 6, which is attached to a human body, withdraws a body fluid from the body. The body fluid sampler 6 mixes the withdrawn body fluid with the diluent introduced thereto through the diluent channel to prepare a diluted body fluid in the sampler. The diluted body fluid thus prepared is transferred through the body fluid channel 9 to the biological component-measuring sensor 8. The transference of the diluted body fluid is carried out by the diluted body fluid-pumping device 11.

Once the diluent-pumping device 10 begins pumping the diluent to the body fluid sampler 6, the first optical sensor 2 outputs detection data and sends them to the controlling unit 4. The diluted body fluid prepared in the body fluid sampler is also measured by the second optical sensor 3, which is disposed on the diluted body fluid channel 9. The second optical sensor 3 outputs detection data and sends them to the controlling unit 4.

The controlling unit 4 judges that the first optical sensor 2 is not properly fitted to the diluent channel 7, when it finds no noise in the detection data received from the first optical sensor 2. Detection data outputted by the first optical sensor 2 always include noise when a diluent flow through the diluent channel 7 to which the first optical sensor 2 is fitted. The controlling unit 4 judges whether a diluent flows through the diluent channel 7, by the inclusion of noise in the detection data.

The controlling unit 4 cancels out noise included in the second detection data received from the second optical sensor 3, utilizing the second detection data received from the second optical sensor 3 and the first detection data from the first optical sensor 2. The basis for the negation of noise included in the second detection data by the first detection data is that the first optical sensor 2 and the second optical sensor 3 are disposed in close proximity to each other and located in a same environment, which exposes both the first and second optical sensors 2, 3 to the same external disturbing factors.

The controlling unit 4 is capable of calculating a dilution of the diluted body fluid from a voltage, which is a detection datum outputted by the second optical sensor 3. The voltage outputted by the second optical sensor 3 when a diluent per se is allowed to flow through the diluted body fluid channel 9 means that the fluid flowing in the channel is a 100% diluent. On the other hand, the voltage outputted by the second optical sensor 3 when a body fluid per se is allowed to flow through the diluted body fluid channel 9 means that the fluid flowing in the channel includes 0% of a diluent. Therefore the dilution of a diluted body fluid flowing through the diluted body fluid channel 9 is known from the second voltage outputted by the second optical sensor 3. Utilizing the first voltage outputted by the first optical sensor 2, this controlling unit 4 cancels out noise and provides a more accurate dilution. Continuous monitoring of the calculated dilution leads to continuous observation of variations in the dilution. The controlling unit 4 judges that an abnormal dilution of a body fluid occurs when variations of the dilution are over a predetermined upper limit or under a predetermined lower limit. Upon making this judgment, the controlling unit sends a command signal to the display 12 and makes it show a warning.

The monitor device according to the present invention may be incorporated into a biological component-measuring device, such as a body fluid-measuring device, which measures components and/or properties of a body fluid included in a diluted body fluid, a body fluid diluted with a diluent. Examples of the biological component-measuring device may include artificial endocrine pancreas devices for measuring a blood sugar level in blood and based on the measurement results supplying insulin to a living organism, dialyzers for dialyzing, urea concentration meters for measuring the urea content included in the body fluids of a living organism, uric acid concentration meters for measuring a uric-acid content in the body fluids of a living organism, sugar concentration meters for measuring lactose and sucrose in the body fluids of a living organism, lactic acid concentration meters for measuring lactic acids such as lactate, glutamic acid concentration meters for measuring the glutamic acid content in the body fluids of a living organism, ammonia concentration meters for measuring an ammonia content in the body fluids of a living organism, and creatinine concentration meters for measuring a creatinine content in the body fluids of a living organism.

Figure 2:
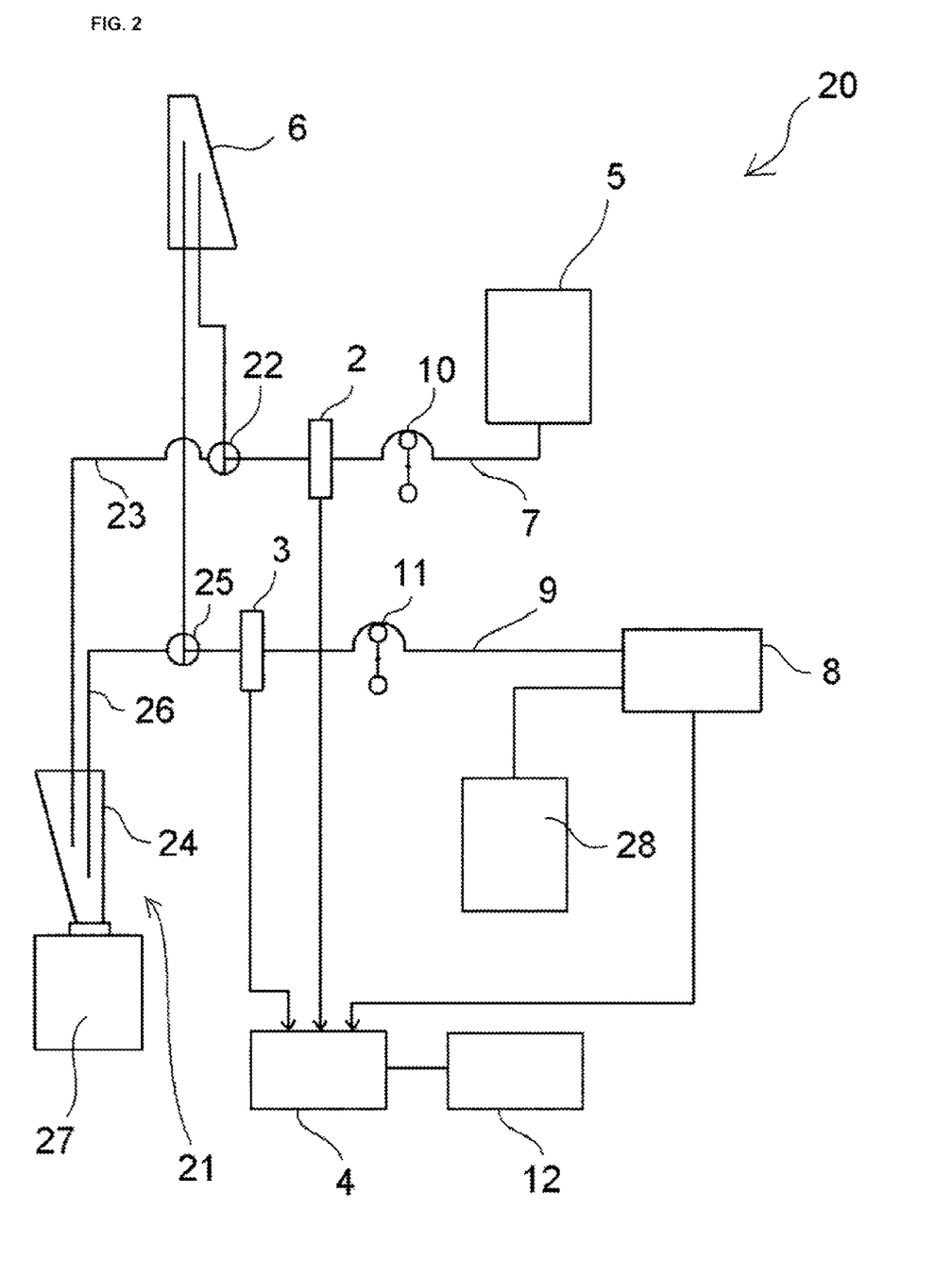
FIG. 2 is an illustration showing an example of the biological component-measuring device according to the present invention.

The biological component-measuring device into which the monitor device according to the present invention is incorporated will be explained herein after. Some of the reference numerals in FIG. 2 are also included in FIG. 1. Members denoted by such reference numerals in FIG. 2 are the same as the members denoted by the same reference numerals in FIG. 1.

A biological component-measuring device 20, which is an example of the biological component-measuring device according to the present invention, includes a diluted standard solution-supplying unit 21 in addition to the monitor device 1, as understood from FIG. 2. The diluted standard solution-supplying unit 21 includes a diluent-supplying channel 23 connected to the diluent channel 7 via a first flow path changeover device 22 that is placed at a location downstream of the first optical sensor 2 fitted to the diluent channel 7; a standard solution-diluting unit 24 where a standard solution is diluted with a diluent supplied thereto through the diluent-supplying channel 23 so that a diluted standard solution is prepared; and a diluted standard solution-drawing channel 26, connected to the diluted body fluid channel 9 via a second flow path changeover device 25 that is placed at a location upstream of the second optical sensor 3 fitted to the diluted body fluid channel 9, for introducing the diluted standard solution prepared in the standard solution-diluting unit 24 into the diluted body fluid channel 9. A standard solution is supplied to the standard solution-diluting unit 24 from a standard solution tank 27. In FIG. 2, reference numeral 28 denotes a waste liquid tank in which a diluted body fluid that has been measured by the biological component-measuring sensor 8 is stored as a waste liquid.

The first flow path changeover device 22 is capable of switching between a flow path in which fluid is not allowed to pass from the first optical sensor 2 to the diluent-supplying channel 23 but allowed to pass from the first optical sensor 2 to the body fluid sampler 6, and a flow path in which fluid is allowed to pass from the first optical sensor 2 to the diluent-supplying channel 23 and not allowed to pass from the first optical sensor 2 to the body fluid sampler 6. Various structures may be employed for this first flow path changeover device as long as they are capable of switching flow paths in this way.

For the second flow path changeover device 25 may be employed the same structure as for the first flow path changeover device 22.

The standard solution-diluting unit 24 dilutes a standard solution stored in the standard solution tank 27 with a diluent brought thereto through the diluent-supplying channel 23 so as to achieve a predetermined dilution. The dilution may be decided by the amount of a diluent per unit time pumped by the diluent-pumping device 10 and that of a diluted body fluid per unit time pumped by the diluted body fluid-pumping device 11.

The standard solution stored in the standard solution tank 27 may be an aqueous solution of a body fluid to be measured, the concentration of which is known, or an aqueous solution of a body fluid to be measured, the properties of which are known. When the biological component-measuring device is an artificial endocrine pancreas device, a typical component to be measured is glucose included in blood. Then a standard solution used in this artificial endocrine pancreas device may be an aqueous solution of glucose whose concentration is known.

The biological component-measuring sensor 8 should have an appropriate structure depending on the kinds of living organisms to be measured, the kinds of target components in a living organism, and target properties, such as pH values, of a living organism. Examples of the biological component-measuring sensor were mentioned in relation to the monitor device.

When the biological component-measuring device according to the present invention is used as an artificial endocrine pancreas device and the monitor device monitors the state of blood withdrawal, the biological component-measuring sensor 8 measures glucose. An example of the biological component-measuring sensor 8 for an artificial endocrine pancreas device may be a biosensor made by coating a carbon electrode with an osmium polymer, drying the coated electrode at room temperature, applying an enzyme solution thereto to make a film layered thereon, and immobilizing the enzyme by a cross-linking agent such as glutaraldehyde. This biosensor causes an oxidation reaction between peroxide and a peroxidase enzyme, which is immobilized in the osmium polymer, and the reaction is followed by reduction reactions between the osmium polymer, the peroxidase and the electrode. The electrode potential during these reactions is 0 mV compared with the electrode potential of the silver-silver chloride electrode. Therefore the utilization of the glucose oxidase for the enzyme for the oxidation reaction leads to a quick detection of glucose and an easy measurement of the concentration thereof. The glucose sensor may include, other than that explained above, a glucose sensor including an osmium (II)-bipyridine complex, one including a ruthenium complex, and a glucose sensor with an electrode modified with a polypyrrole into which a tris-osmium complex is immobilized. Among these various glucose sensors, the biosensor employing the osmium polymer is preferable. Suitable glucose sensors are film sensors having a work electrode of platinum, silver or carbon, and an enzyme film of an osmium polymer impregnated with peroxidase.

The monitor device and biological component-measuring device according to the present invention may be structured so that they are capable of dealing with one or more measurable components or properties of a living organism. When two or more components or properties of a living organism are measured, the devices should be equipped with two or more kinds of body fluid-measuring sensors, such as biosensors, in the diluted body fluid channel, through which a diluted body fluid, or a body fluid diluted with a diluent, is transferred. Another way to measure several components and/or properties of a living organism may be to make the diluted body fluid channel branch off and to provide each branch channel with one or more body fluid-measuring sensors.

The controlling unit 4 of the biological component-measuring device 20 calculates the concentration of a target component in a body fluid and/or a property of a body fluid included in a diluted body fluid flowing through the diluted body fluid channel 9, from detection data outputted by the body fluid-measuring sensor 8. The controlling unit also does calculation of the dilution, computations necessary to calibrate the body fluid-measuring sensor 8, and some other calculations.

Calibration of the body fluid-measuring sensor 8 in the biological component-measuring device 20 may be carried out in the following way.

A standard solution having a known concentration is stored in the standard solution tank 27. When this biological component-measuring device 20 is an artificial endocrine pancreas device, an aqueous glucose solution having a known concentration, for example 200 mg/dL, of glucose is stored as standard solution in the standard solution tank 27.

When a standard solution, for example the standard solution having the known concentration written above, is allowed to flow through the standard solution channel 9, detection data of the standard solution measured by the biological component-measuring device 8 are obtained. Also, when a diluted standard solution, prepared by diluting the standard solution with a diluent to a predetermined dilution, is allowed to flow through the diluted body fluid channel 9, detection data of the diluted standard solution measured by the biological component-measuring device 8 are obtained. A calibration curve can be prepared from the detection data of the standard solution and those of the diluted standard solution. The controlling unit 4 is capable of calculating a reference datum when the concentration of a solute is zero based on the calibration curve, which makes it possible carry out a zero point calibration. The detection datum obtained by the biological component-measuring device 8 when a sole diluent, which does not include a body fluid, is allowed to flow through the diluted body fluid channel 9 also provides the reference datum when the concentration of a solute is zero.

We will explain the operation of an artificial endocrine pancreas device, an example of the biological component-measuring device 20 that is structured in the way described hereinbefore, referring to FIG. 2, in the following. In FIG. 20, reference numeral 20 denotes an artificial endocrine pancreas device, 11 a diluted blood-pumping device, 9 a diluted blood channel, 8 a glucose sensor, and 6 a blood sampler.

When a blood sugar level is measured by an artificial endocrine pancreas device 20, a blood sampler 6 is fitted to a patient. A catheter is normally used as blood sampler 6, so a catheter is positioned in a vein of the patient. Upon an actuation of the diluent-pumping device 10, a diluent is driven out of the diluent tank 5 to the blood sampler 6 through the diluent channel 7. Light transmitted or reflected by the diluent flowing through the diluent channel 7 are measured by the first optical sensor 2, and voltages as measured data is outputted and sent to the controlling unit 4.

Upon an actuation of the diluted blood-pumping device 11, blood of the patient is withdrawn to the blood sampler 6. The blood withdrawn from the patient is diluted with a supplied diluent in the blood sampler 6. The dilution may be decided by, for example, the pumping speed of the diluted blood-pumping device 11 and that of the diluent-pumping device 10. Light transmitted or reflected by the diluted blood flowing through the diluted blood channel 9 is measured by the second optical sensor 3, and voltages as measured data are outputted and sent to the controlling unit 4.

The glucose component of the diluted blood that is transferred through the diluted blood channel 9 is measured by the glucose sensor 8, and the measured datum is sent to the controlling unit 4.

The controlling unit calculates the concentration of glucose from the measured datum received from the glucose sensor 8. The datum when the concentration of glucose is zero may be obtained from the measured datum of, for example, a sole diluent sent to the glucose sensor 8 by the diluted blood-pumping device 11.

Measurement of the concentration of glucose in a diluted blood by the glucose sensor 8 sometimes experiences measured data off the baseline as time lapses. On such occasions, calibration should be carried out at an appropriate time. Calibration of the glucose sensor 8 may be carried out in the following way: The first flow path changeover device 22 is switched so that a diluent in the diluent tank 5 is sent to the standard solution-diluting unit 24 via the device 22. The second flow path changeover device 25 is also switched so that a diluted standard solution, prepared in the standard solution-diluting unit 24, is allowed to flow through the diluted blood channel 9. The concentration of glucose in the diluent and that of glucose in the diluted standard solution are measured by the glucose sensor 8, and the measured data are sent to the controlling unit 4. The calibration is thus carried out.

Variations in the dilution of a diluted blood may be monitored by the monitor device 1, which is incorporated into the artificial endocrine pancreas device 20.

As explained hereinbefore, the artificial endocrine pancreas device 20 is capable of continuously measuring the concentration of glucose in blood and detecting abnormalities in blood withdrawal by monitoring the dilution of blood. The artificial endocrine pancreas device is also capable of calibrating the glucose sensor 8, which leads to an accurate measurement of the concentration of glucose. Therefore the device is capable of dosing a patient with a proper amount of insulin.

The monitor device, which is incorporated into the artificial endocrine pancreas device, doubles as a safety device, because it is capable of judging whether the switching device works properly when the operation mode is switched from calibration to measurement of the blood sugar level of a patient. It can be said that the monitor device is a safety device which observes biological component-measuring devices into which the monitor device is incorporated, such as artificial endocrine pancreas devices. When a biological component-measuring device, such as an artificial endocrine pancreas device, into which the monitor device is not incorporated, is used, measured values of a target component are sometimes different from real values, due to some reasons including leakage of a small amount of the standard solution into the diluted body fluid channel. Therefore there is a probability that the doctor may make an erroneous diagnosis based on wrong measurement results about the conditions of the patient's body fluid. On the other hand, the devices according to the present invention are capable of providing accurate information about the measured body fluid of a patient, which will not lead to an erroneous diagnosis by the doctor. The monitor device and the biological component-measuring device into which the monitor device is incorporated are very important as devices which ensure safety of patients during a long-time measurement of their body fluids.

We claim:

1. A monitor device including:
   a first optical sensor disposed on a diluent channel through which a diluent is introduced into a body fluid sampler for withdrawing a body fluid;
   a second optical sensor disposed on a diluted body fluid channel through which a diluted body fluid is transferred to a biological component-measuring sensor, and in close proximity to the first optical sensor, wherein the diluted body fluid is prepared by mixing the body fluid withdrawn by the body fluid sampler with the diluent; and
   a controller configured for judging whether variations in a dilution ratio to which the body fluid is diluted with the diluent are within predetermined limits, based on first detection data from the first optical sensor and second detection data from the second optical sensor.

2. A biological component-measuring device including the monitor device according to claim 1.

3. The living organism-measuring biological component-measuring device according to claim 2 wherein the living organism-measuring biological component-measuring device is applied to an artificial endocrine pancreas device.

4. The monitor device according to claim 1, wherein the second optical sensor disposed in close proximity to the first optical sensor so that the first and second optical sensors are exposed to substantially the same external disturbing factor.

5. The monitor device according to claim 4, wherein the controller is configured to cancel a noise caused by the external disturbing factor in the second detection data from the second optical sensor based on the first detection data from the first optical sensor.

6. The monitor device according to claim 1, wherein the controller is configured for judging the dilution ratio variations when determining that the diluent flows through the diluent channel.

7. A biological component-measuring device comprising:
a monitor device comprising:
   a first optical sensor disposed on a diluent channel through which a diluent is introduced into a body fluid sampler for withdrawing a body fluid;
   a second optical sensor disposed on a diluted body fluid channel through which a diluted body fluid is transferred to a biological component-measuring sensor, and in close proximity to the first optical sensor, wherein the diluted body fluid is prepared by mixing the body fluid withdrawn by the body fluid sampler with the diluent; and
   a controller configured for judging whether variations in a dilution to which the body fluid is diluted with the diluent are within predetermined limits, based on first detection data outputted by the first optical sensor and second detection data outputted by the second optical sensor; and
a diluted standard solution-supplying unit comprising:
   a diluent-supplying channel branched from the diluent channel via a first flow path changeover device at a location downstream of the first optical sensor;
   a standard solution-diluting unit for diluting a standard solution with the diluent introduced thereto through the diluent-supplying channel to prepare a diluted standard unit; and
   a diluted standard solution-drawing channel branched from the diluted body fluid channel via a second flow path changeover device at a location upstream of the second optical sensor wherein the diluted standard solution prepared in the standard solution-diluting unit is drawn and sent to the diluted body fluid channel through the diluted standard solution-drawing channel.

8. The biological component-measuring device according to claim 7 wherein the biological component-measuring device is applied to an artificial endocrine pancreas device.

9. A biological component-measuring device comprising:
a biological component-measuring sensor for a body fluid;
a diluent channel connected to a diluent tank for allowing only a diluent to flow therethrough;
a body fluid sampler, connected to the diluent channel, for obtaining the body fluid to dilute the body fluid with the diluent;
a diluted body fluid channel, connected to the body fluid sample, for providing the diluted body fluid to the biological component-measuring sensor;
a first optical sensor disposed on the diluent channel;
a second optical sensor disposed on the diluted body fluid channel, the second optical sensor being disposed in close proximity to the first optical sensor; and
a controller for judging whether variations in a dilution ratio of the diluent and the body fluid based on outputs of the first and second optical sensors.

\* \* \* \* \*